United States Patent [19]

Clebant et al.

[11] 4,009,606
[45] Mar. 1, 1977

[54] DEVICE FOR THE STUDY OF MATERIALS SUBJECTED TO ALTERNATE TENSILE AND COMPRESSIVE TESTS

[75] Inventors: Jean-Claude Clebant, Carbon Blanc; Jean-Claude Fecan, Merignac, both of France

[73] Assignee: Commissariat a l'Energie Atomique, Paris, France

[22] Filed: Jan. 21, 1976

[21] Appl. No.: 650,918

[30] Foreign Application Priority Data

Jan. 27, 1975 France .............................. 75.02444

[52] U.S. Cl. ................................................. 73/91
[51] Int. Cl.² ........................................ G01N 3/32
[58] Field of Search .................. 73/91, 93, 67.3, 92

[56] References Cited

UNITED STATES PATENTS

| | | | |
|---|---|---|---|
| 3,187,565 | 6/1965 | Kreiskorte et al. ................. | 73/91 X |
| 3,214,969 | 11/1965 | Swanson ................. | 73/91 |
| 3,699,808 | 10/1972 | Ford et al. ................. | 73/91 |

*Primary Examiner*—Jerry W. Myracle
*Attorney, Agent, or Firm*—William R. Woodward

[57] ABSTRACT

A device for subjecting n (n ≥ 1) test specimens to alternate tensile and compressive stresses comprises an excitation source having a horizontal axis of displacement and a guide rod which is capable of free translational displacement along a horizontal axis. The guide rod is rigidly fixed at one end to the exciter and provided at the other end with means for clamping the ends of n test specimens. A massive part is provided with nozzles for the injection of a gas under pressure and with n horizontal bearing blocks constituting gas bearings for n cylindrical and horizontal masses to which the other ends of the test specimens are secured.

7 Claims, 2 Drawing Figures

DEVICE FOR THE STUDY OF MATERIALS SUBJECTED TO ALTERNATE TENSILE AND COMPRESSIVE TESTS

This invention relates to a device for studying materials which are subjected to alternate tensile and compressive stresses.

It is known that a mechanical part can be subjected in a general manner to two types of stress: one may refer in a first instance to a static load, which is understood to mean that the direction of application of the stress to which the part is subjected always has the same direction (for example a tensile stress or a compressive stress). Alternatively one may refer to dynamic loads in which the force applied to the mechanical part varies in direction or, in other words, in which alternate tensile and compressive stresses are applied.

In the event that the parts are subjected to vibrations, alternate stresses are clearly applied. In order to determine the dimensions of such parts, it is obviously necessary to know the characteristics of resistance of the material to said alternate stresses.

In more exact terms, it is necessary to know the fatigue curve of said material as a function of the number of stress cycles to which it is subjected.

In order to study the fatigue characteristics of a material, a rigid test piece is formed of said material and subjected to alternate tensile and compressive stresses by means of a device of special design.

Machines for subjecting test specimens to alternate stresses are already known. Some of these machines are specially designed to perform static tests either in tension or in compression and may be employed if necessary in the field of vibrations provided that they are permitted to remain within a low-frequency range (frequencies below 50 cycles per second). A further major disadvantage of these tensile testing machines is that they are highly unsuitable for tests of long duration since the endurance of the machines themselves is at risk during these tests.

It is known that a material has to be subjected to about a hundred different tests in order to obtain the fatigue curve of said material and that some tests can consist of several tens of millions of cycles. It is clearly a considerable advantage to make use of a machine which is capable of testing at a much higher rate and permits a utilization frequency which can attain 500 c/s in order to reduce the time-duration of tests.

In order to be able to carry out fatigue tests at high frequencies and under various types of stresses, it is found necessary to employ an electrodynamic exciter as excitation source. The main difficulty lies in the fact that the test specimen cannot be subjected to prestress at the time of mounting in the testing apparatus.

The precise aim of the present invention is to provide a device for studying materials subjected to alternate tensile and compressive stresses which overcomes the disadvantages mentioned in the foregoing and makes it possible in particular to employ a device which is readily adaptable to a conventional electrodynamic exciter.

The device for subjecting n (n ≥ 1) test specimens of a material to alternate tensile and compressive stresses essentially comprises an excitation source having a horizontal axis of displacement, a guide rod in which one end of said rod is rigidly fixed to said exciter and the other end is fitted with n elements for securing one of the ends of the n test specimens, said rod being guided so as to be capable of free translational displacement along a horizontal axis and a massive part provided with n horizontal bearing blocks and with nozzles for the injection of a gas under pressure, said n bearing blocks being thus intended to constitute gas bearings for n cylindrical masses which each have a horizontal axis, said masses being provided on that face which is directed towards said rod with an element for securing the other end of one of the n test specimens.

In a preferred embodiment, each mass is provided with means for preventing rotational displacement of said mass about its axis.

In the case of each mass, said means are preferably constituted by at least one flat surface formed on the lateral face of said mass, said flat surface or surfaces being intended to cooperate with an equal number of flat surfaces formed on the bearing face of the corresponding bearing block.

In accordance with another characteristic feature, said massive part is provided with n cylindrical bores each having a horizontal axis and a substantially circular cross-section, said axes being spaced at uniform intervals over a cylindrical surface having a circular cross-section and a horizontal axis of revolution which coincides with that of said rod.

A more complete understanding of the invention will be obtained from the following description of a number of practical modes of execution which are given by way of example without any limitation being implied, reference being made to the accompanying drawings, in which.

Figure 1:
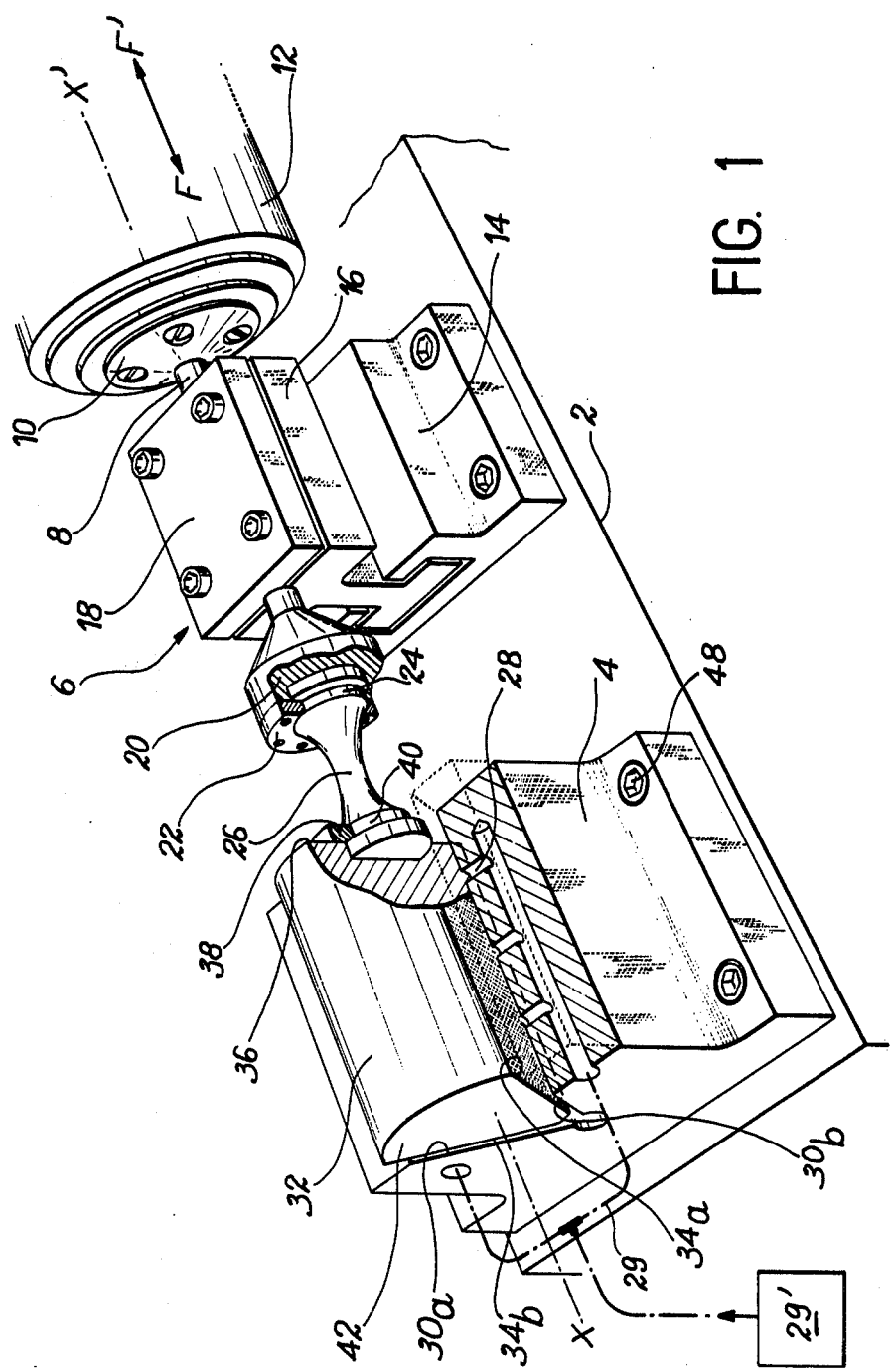
FIG. 1 is a perspective view of a device for studying materials and testing a single test specimen.

Referring to FIG. 1, it is observed that the complete device rests on a stationary table 2. There are securely fixed on said table a bearing block 4 which will be described hereinafter and a guiding system 6.

The bearing block 4 and the guiding system 6 are fixed on the table 2 so as to have a common horizontal axis X-X'. The guiding system 6 can be of any desired type and serves to guide the rod 8. The end plate or drive plate 10 of said rod is rigidly fixed to the drive plate unit 12 of the electrodynamic exciter. The guiding system 6 comprises a stationary guide block 14 which is rigidly fixed to the table 2 and a movable frame 16 which is guided in translational motion with respect to the guide block 14 in the direction of the axis X-X'.

The guiding system 6 may consist in particular of a gas bearing which is coaxial with the bearing block 4. The alignment of said bearing block is preferably established by design and rotational locking is obtained by methods which are identical with those mentioned in the case of the movable mass.

The frame is provided with elements 18 for securing the rod 8 to the movable portion 16. At the other end 20, the rod 8 is provided with flanges 22 for joining this latter to the head 24 of the specimen 26 to be tested.

The flanges 22 are of known type and permit perfect centering of the axis of the test specimen with respect to the axis of the rod 8.

The bearing block 4 together with its nozzles 28 for the injection of gas under pressure constitutes a gas bearing. The nozzles are connected by means of the pipe 29 to a source 29' of gas under pressure.

The internal section of said bearing block is of cylindrical shape having any desired director-section is provided, for example, with two flat surfaces 30a and 30b.

A loading mass 32 which has the shape of a cylinder having any desired director-line and a horizontal axis X-X' is capable of displacement within the bearing block 4. In the example which is illustrated, the loading mass 32a has the shape of a cylindrical sector provided with two flat surfaces 34a and 34b which correspond to the flat surfaces 30a and 30b. The loading mass 32 is provided on the face 36 which is directed towards the rod 8 with clamping flanges 38 which grip and permit centering of the head 40 of the test specimen 26. It is therefore apparent that the assembly formed by the rod 8 of the test specimen 26 and the loading mass 32 constitutes a moving system which is capable of horizontal translational motion along the axis X-X'.

These movements of translation in the direction of the arrows F and F' are imparted by the exciter 12. The air bearing serves to overcome two types of difficulty:

it ensures a high degree of accuracy in the definition of the axis X-X' of translational displacement;

by virtue of its mobility, the bearing block makes it possible to ensure very accurate alignment of the axes of assembly and therefore to subject the test specimen to working stress solely in the tension-compression mode. Furthermore, the use of the gas bearing permits a considerable reduction of the friction forces of the loading mass 32 with respect to its support.

In fact, a bearing block of this type is subjected under the conditions of use in fatigue tests, to negligible friction forces which thus make it possible to obtain very simple experimental conditions, the only variable parameter to be taken into consideration being the law of acceleration of the exciter.

The bearing block 4 makes it possible to ensure excellent guiding in the direction X-X' as well as operational safety. Moreover, the bearing block is practically proof against wear (integrity in time).

In order to prevent rotational oscillations about the axis X-X', the mass 32 is provided with two flat surfaces which thus prevent movements of rotation.

It would also be possible to contemplate other devices for rotational locking by means of flexible strips which possess a high degree of rigidity with respect to movements of rotation and a very low degree of stiffness with respect to the main movement of translation (the movement of tension and compression).

Figure 2:
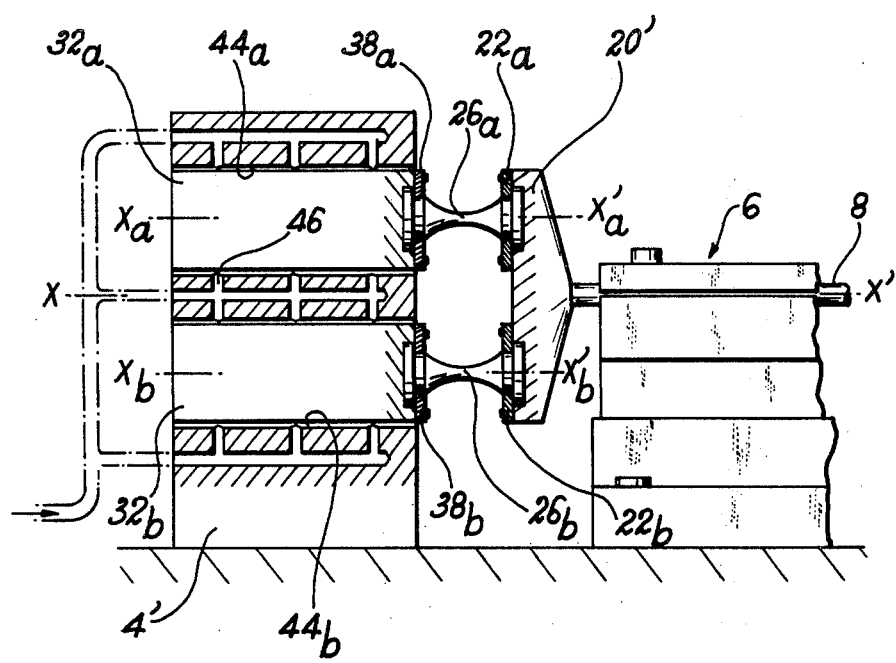
FIG. 2 is a vertical sectional view of a device for testing four test specimens simultaneously.

In the alternative embodiment shown in FIG. 2, a number of test specimens can be tested simultaneously. In the particular case which is illustrated, this number is equal to four, only two test specimens being shown in the section plane.

The end 20' of the rod 8 is provided with four clamping flanges 22a, 22b which serve to grip one of the heads of the test specimens 26a and 26b.

It is readily apparent that the axes $X_a$ $X'_a$ and $X_b$ $X'_b$ of the test specimens are parallel to the axis X-X' of the rod 8.

There are four loading masses 32a, 32b, each mass being associated with one of the test specimens.

There corresponds to each mass a clamping flange 38a, 38b which serves to secure the second end of each test specimen.

The bearing block 4 is replaced in this case by a member 4' provided with bores which are equal in number to the loading masses. In this particular case, there are therefore four bores designated respectively by the references 44a, 44b.

It is clearly apparent that the bores 44a and 44b have exactly the same shape as the loading masses 32a and 32b.

The loading masses 32a and 32b are cylinders which may or may not have a circular cross-section and the same accordingly applies to the bores 44a and 44b. In the case of a circular cross-section, a rotational locking system must be provided on each of the loading masses 32a and 32b.

The bores 44a and 44b clearly have a diameter which is very slightly larger than that of the corresponding loading members so as to provide a clearance which permits the introduction of an air cushion for each loading mass. Each bore 44 is supplied with air under pressure through injection nozzles such as the nozzle 46.

Provision can be made for a variable number of nozzles and said nozzles are located at uniform intervals along the length of the loading masses and at the periphery of these latter. The size of the loading mass and of its bearing block is defined as a function of the test specimens and is therefore established a priori; on the other hand, the number of masses is therefore adapted to the installation as shown in FIG. 2.

In order to prevent the introduction of any extraneous stress after failure of one of the test specimens, a detector serves to stop the machine as soon as a specimen has failed, that is to say as soon as a loading mass departs from the normal range of displacement. It is then only necessary to change the failed specimen and resume testing.

The device described in the foregoing offers the following simultaneous advantages:

the test specimens are subjected to working stress solely in the tension-compression mode, no prestress is applied in the zone of fracture of the test specimen, the applied stresses are perfectly determined, the device makes it possible to study fatigue of materials by applying various types of stresses (harmonic vibrations at fixed or variable frequencies, random vibrations, impacts), tests are performed very rapidly.

What we claim is:

1. A device for subjecting $n$ ($n \geq 1$) test specimens of a material to alternate tensile and compressive stresses, wherein said device comprises an excitation source having a horizontal axis of displacement, a guide rod in which one end of said rod is rigidly fixed to said exciter and the other end is fitted with $n$ elements for securing one of the ends of the $n$ test specimens, said rod being guided so as to be capable of free translational displacement along a horizontal axis and a massive part provided with $n$ horizontal bearing blocks and with nozzles for the injection of a gas under pressure, said $n$ bearing blocks being thus intended to constitute gas bearings for $n$ cylindrical masses which each have a horizontal axis, said masses being provided on that face which is directed towards said rod with an element for securing the other end of one of the $n$ test specimens.

2. A device according to claim 1, wherein the excitation source is an electrodynamic exciter.

3. A device according to claim 1, wherein each mass is provided with means for preventing rotational displacement of said mass about its axis.

4. A device according to claim 3 wherein, in the case of each mass, said means are constituted by at least one flat surface formed on the lateral face of said mass, said flat surface or surfaces being intended to cooperate with an equal number of flat surfaces formed on the bearing face of the corresponding bearing block.

5. A device according to claim 4, wherein said massive part is provided with $n$ cylindrical bores each having a horizontal axis and any desired cross-section, said axes being spaced at uniform intervals over a cylindrical surface having an adapted cross-section and a horizontal axis which coincides with that of said rod.

6. A device according to claim 5, wherein the system for guiding the member which applies the load to the test specimen is provided by a gas bearing mounted in coaxial relation to the bearing which supports the movable mass.

7. A device according to claim 1, wherein the system for guiding the member which applies the load to the test specimen is provided by a gas bearing mounted in coaxial relation to the bearing which supports the movable mass.

* * * * *